(12) United States Patent
Mayr et al.

(10) Patent No.: US 8,128,696 B2
(45) Date of Patent: Mar. 6, 2012

(54) SYSTEM AND IMPLANT FOR LIGAMENT RECONSTRUCTION OR BONE RECONSTRUCTION

(75) Inventors: Hermann Mayr, Grosshesselohe (DE); Giancarlo Rizzoli, Solothurn (CH)

(73) Assignee: Hermann Mayr, Grosshesselohe (DE)

( * ) Notice: Subject to any disclaimer, the term of this patent is extended or adjusted under 35 U.S.C. 154(b) by 566 days.

(21) Appl. No.: 11/920,324

(22) PCT Filed: May 11, 2005

(86) PCT No.: PCT/EP2005/005089
§ 371 (c)(1),
(2), (4) Date: Apr. 1, 2009

(87) PCT Pub. No.: WO2006/119789
PCT Pub. Date: Nov. 16, 2006

(65) Prior Publication Data
US 2009/0222090 A1    Sep. 3, 2009

(51) Int. Cl.
*A61F 2/08*    (2006.01)
(52) U.S. Cl. .................................... 623/13.14
(58) Field of Classification Search ............ 623/16.11, 623/23.56–23.62, 13.11, 13.14
See application file for complete search history.

(56) References Cited

U.S. PATENT DOCUMENTS

| | | |
|---|---|---|
| 4,629,464 A | 12/1986 | Takata et al. |
| 5,084,050 A | 1/1992 | Draenert |
| 5,152,791 A | 10/1992 | Hakamatsuka et al. |
| 5,262,166 A * | 11/1993 | Liu et al. .................. 424/423 |
| 5,522,895 A | 6/1996 | Mikos |
| 5,676,699 A * | 10/1997 | Gogolewski et al. ...... 623/16.11 |
| 6,013,853 A | 1/2000 | Athanasiou et al. |
| 6,346,123 B1 | 2/2002 | McKay |
| 6,458,148 B1 * | 10/2002 | Dauner et al. .............. 606/228 |
| 6,905,516 B1 * | 6/2005 | Lemaitre et al. ........... 623/23.56 |
| 7,241,732 B2 * | 7/2007 | Puzas ......................... 514/16.6 |
| 7,534,451 B2 * | 5/2009 | Erbe et al. .................. 424/484 |
| 7,776,073 B2 * | 8/2010 | Serhan et al. .............. 606/279 |
| 2002/0106393 A1 | 8/2002 | Bianchi et al. |
| 2003/0180344 A1 * | 9/2003 | Wise et al. ................. 424/423 |
| 2004/0034434 A1 * | 2/2004 | Evans et al. ............... 623/23.51 |
| 2004/0126405 A1 * | 7/2004 | Sahatjian et al. .......... 424/423 |
| 2004/0193270 A1 | 9/2004 | DiMauro et al. |
| 2009/0017095 A1 * | 1/2009 | Barnouin et al. ........... 424/426 |
| 2009/0048145 A1 * | 2/2009 | Hellerbrand et al. ......... 514/2 |

FOREIGN PATENT DOCUMENTS

| | | |
|---|---|---|
| WO | 01/68004 | 9/2001 |
| WO | 03/055418 | 7/2003 |

* cited by examiner

*Primary Examiner* — Suzette J Gherbi
(74) *Attorney, Agent, or Firm* — Dilworth & Barrese, LLP.

(57) ABSTRACT

An implant (5) for ligament and/or bone reconstruction is composed of biodegradable material suitable to be remodeled into vital bone and having mechanical strength for securely fixing a ligament in a bore or hole in bone with a press or form fit and/or reshaping a collapsed surface of bone into original shape. A surgical instrument (9) for ligament and/or bone reconstruction can be used to insert the implant (5) into bone and has a shaft member (3) having a first end (11), a second end and a longitudinal bore (15) having an inner diameter and pushing member (4) having a first end, second end and piston (16) in turn having an outer diameter smaller than or equal to inner diameter of the bore (10) so that the piston (16) of the pushing member (4) can be slidably arranged within the longitudinal bore (10).

21 Claims, 6 Drawing Sheets

SYSTEM AND IMPLANT FOR LIGAMENT RECONSTRUCTION OR BONE RECONSTRUCTION

FIELD AND BACKGROUND OF THE INVENTION

This invention relates to systems and implants for ligament reconstruction or bone reconstruction.

Reconstructions of the cruciate ligaments are among the most frequently performed procedures in knee surgery nowadays. The most common method for re-constructing a torn cruciate ligament involves a bone-patellar tendon graft or a semitendinous graft, which is frequently fixed with metal (e.g. titanium or stainless steel) interference screws. The metal interference screws offer the advantage of a permanent implant with adequate mechanical strength. Sharp threads of the metallic interference screws may harm the transplant. In addition, years after the cruciate ligament reconstruction a revision is difficult to realize due to a bony sheating of the metal implants and often is associated with iatrogen damage.

Alternatively, resorbable interference screws made from PLLA, PDLLA, PLLA/TCP (e.g. 70%/30%) have been used with specially designed threads in order not to cut the tendon transplant. However, drawbacks such as loosening fixation, bone resorption and inflammatory reactions have been reported in literature.

In a different common method, the semitendinous tendon is used as a transplant for the reconstruction of the cruciate ligaments. It is often attached with an inter-connection cord using a fixation distant to the articular. Due to the length and the polynominality of the reconstruction, the fixation may result in deterioration of stiffness and micro movements in the bone channel. Proximal articular fixation systems for semitendinous plasty are performed by inserting a transcondylar pin made of metal or PLLA. Beside the drawbacks of the used materials tunnel enlargement of the drilling tunnel (tunnel enlargement) can be observed in some cases.

The present invention also relates to systems and implants for bone reconstruction which may be necessary if a vital bone structure has collapsed due to too high loads. According to the prior art, a collapsed joint is reconstructed by drilling a bore from a side of the bone which is opposite to the collapsed surface. The collapsed surface is then reduced into the correct anatomical position by introducing a pestle into the bore and by pushing this pestle against the collapsed surface. After the original shape of the collapsed surface has been reestablished, the remaining void under the reshaped surface is filled by a bone replacement material. An example for such a bone replacement material is a cement material as for example described in U.S. Pat. No. 6,733,582 B1. The advantage of this material is that it is biodegradable and is replaced by vital bone structure over the time. However, the replacement material is restricted to applications with minor loadings, because it has a high porosity and contains macro holes in the size of 100 to 500 micrometers which are necessary in order to achieve a fast ingrowth of the vital bone structure.

OBJECTS AND SUMMARY OF THE INVENTION

It is the primary object of the present invention to provide a surgical instrument a system and an implant for ligament reconstruction in order to achieve an improved mechanical strength of the ligament bone connection over the healing period. Further, an early rehabilitation should be achieved.

This object and other objects are achieved by an implant, a surgical instrument and system described herein. Advantageous embodiments of the invention are also described herein.

The inventive implant is a biodegradable material which is suitable to be remodeled into vital bone, and which has a mechanical strength for securely fixing a ligament in a bore or hole of a bone by means of press fit or form fit. In this patent application, the property of the biodegradable material to be remodeled into vital bone means that new vital bone is formed simultaneously as the implant material degrades by cellular activity. Osteoblasts fill the lacunae, thus synthesizing extracellular matrix which is subsequently calcified.

For reconstructing a ligament according to the present invention, the practitioner drills a bore into the bone. A natural ligament plasty (autograft, allograft or xenograft) with optional small bone blocks at one or both ends or a synthetic ligament is then inserted into the bore. The ligament is pressed to the side walls of the bore by means of a pestle or trocar so that the ligament which has viscoelastic properties, as well as the surrounding bone structure expand in radial direction. The inventive implant is then pressed into the bore in order to securely fix the ligament to the bone by press fit or form fit. The other end of the ligament may finally be fixed to another bone by means of the inventive implant or by means of conventional methods.

The implantation of the inventive implant is simple and can easily be reproduced also by practitioners with little experience in this field. The implant achieves a tensile force to failure of the ligament bone connection which is comparable or equal to a conventional fixation with interference screws. The mechanical properties of the ligament bone connection are sufficient during the complete healing phase and allow early rehabilitation. The risk of a critical loss of mechanical strength over healing period is reduced.

For pressing the implant into the bore for securely fixing the ligament, the inventive implant is designed to have a sufficient mechanical strength. The mechanical strength is sufficient to resist the pressure of a surgical instrument for pressing the implant into the bore. Therefore, the implant preferably has a compression strength of at least 50 $N/mm^2$, in particular at least 80 $N/mm^2$. Therefore, in case of a diameter of the implant of 7 mm, a force of up to 1900 N or 3000 N, respectively, may be applied to the implant for inserting the implant into the bore and for securely fixing the ligament by press fit or form fit. In view of theses forces, the inventive implant is also designed to resist shear stress of preferably at least 50 $N/mm^2$ so that the side walls of the implant are not sheared off during insertion into the bore.

The biodegradable material of the inventive implant may have a micro pore structure with an average diameter ranging from 1 to 50 micrometers, in particular from 2 to 10 micrometers. The micro porosity accelerates the remodeling process by increasing the surface area an allowing for circulation of body fluids. Therefore, the porosity of the biodegradable material should be tailored to the desired period of biodegradation within a vital bone. On the other hand, the porosity of the biodegradable material is tailored to the mechanical strength required for securely fixing a ligament in a bore or hole by means of press fit or form fit. In order to achieve this mechanical strength, a porosity ranging from 25% to 50% by volume is preferred, in particular a porosity of about 40% by volume. Preferably, at least part or all of the biodegradable material has no macro pores, which are defined in this patent application as having a diameter ranging from 100 to 500 micrometers.

The micro pore structure is also advantageous in view of the mechanical properties of the implant. The maximum tension stress at the end of a micro crack is reduced, because the radius of a micro pore is larger than the radius at the end of a crack in case of a material without micro pores. As a result, the tendency of a propagation of micro cracks is significantly reduced, in particular during the insertion of the implant. Since the preferred biodegradable material of the present invention is a ceramic material which is highly fragile per se, the micro pore structure is a measure to reduce the risk that the implant breaks during implantation due to the high compression force in order to press the implant into the bore of the bone.

In order to optimize the mechanical properties and the remodeling characteristics, the biodegradable material may have a gradient porosity, e.g. lower porosity and a higher mechanical strength at the outer surface of the implant, and a higher porosity at the center of the implant. With that, a quicker remodeling of vital bone at the end of the healing process and a quicker rehabilitation is achieved.

According to the present invention, the implant materials are comprised of sintered or not sintered microporous ceramics such as hydroxyapatite, tricalcium phosphate, brushite, calcium sulfates, bioglass and combinations thereof. The preferred biodegradable material is β-tricalcium phosphate ($\beta$-$Ca_3(PO_4)_2$). This ceramic material already has been suggested as material for filing voids in bones. However, since this material is optimized for fast biodegradation, it contains macro pores resulting in a low strength material. The use of β-tricalcium phosphate has been restricted according to the prior art to applications with minor loadings.

The implant preferably consists only or at least 60% by weight, in particular at least 75% by weight of said biodegradable material which is suitable for remodeling into bone. The biodegradable material for remodeling into bone may be mixed or coated with other degradable materials such as polysaccharides, dextran, starch, alginate, chitosan, proteins, albumin, collagen, gelatin, polyesters, different types of lactid acid, poly(glycolide) (PGA), poly(ϵ-caprolactone) (PCL), poly(β-hydroxyalkanoates) such as poly(β-hydroxybutyrate) (PHB) and poly(β-hydroxyvalerate) (PHV), polyether-ester, poly(p-dioxanone) (PDO), polycarbonates, poly(trimethylene carbonate) (PTMC), poly(desaminotyrosyl tyrosine [ethyl ester]carbonate) (PDTE), poly(amino acids), tyrosine-derived polycarbonates and polyarylates, poly(anhydrides), poly(SA-HAD anhydride), where SA is sebacic acid and HAD is hexadecandioic acid, poly(orthoesters), polyphosphoesters, polyphosphazenes, polyurethanes, polyesteramides, polyalkylenoxalates and polyalkylcyanoacrylates. Such a composition of materials can be designed to further improve the mechanical properties of the implant for specific applications. In particular, a composition with polymers reduces the fragility of the biodegradable material which is suitable for remodeling into bone.

The material of the implant may further contain one or more agents for facilitating osteogenesis. For this purpose, peptides, proteins, hormones, oligonucleotides, nucleic acids, steroids, antibiotics, antiseptics and vaccines are particularly suitable. The agent may be contained in or on the surface of the micro pore structure of the biodegradable material or in or on a polymer as a carrier for the agent in order to achieve a controlled release characteristic due to the degradation of the polymer and/or of the ceramic.

The implant of the present invention has preferably a cylindrical shape. With that, a maximum friction at the side walls of the implant is achieved so that pulling out of the ligament form the bore is avoided. However, also a conical shape is possible, in particular in case of a retrograde fixation of a ligament, i.e. at a side of the bone which is opposite to the joint. For that, an angle of the side walls with respect to the center axis of the implant of 2° to 15° is preferred, in particular about 7° to 8°.

The implant may further have circumferential or longitudinal grooves or be designed in shape of a screw or of a fir tree in order to locally have an increased pressure between the implant and the surrounding vital bone structure. Such a locally increased pressure promotes the ingrowth of vital bone into the implant.

In view of the mechanical properties of the implant, it is preferred that the implant has no internal bores having a length exceeding 500 micrometers, and no bores as, for example, necessary with conventional implants in the shape of a dowel for fixing screws. On the other side, the implant of the present invention may be provided with an internal bore extending through the entire implant at its center axis in order to cooperate with a guide wire during implantation. This internal bore should have a small diameter in order not to reduce the mechanical properties of the implant, but to sufficiently support the implant over the guide wire in order to avoid a misalignment of the implant within the bore of the bone.

According to the present invention, the implant is preferably performed by means of a surgical instrument comprising a shaft member having a first end, a second end and a longitudinal bore, wherein the longitudinal bore has an inner diameter, and a pushing member having a first end, a second end and a piston, wherein the piston has an outer diameter which is smaller or equal than the inner diameter of the longitudinal bore so that the piston of the pushing member can be slidably arranged within the longitudinal bore.

With this surgical instrument, the implant can be inserted into the longitudinal bore of the shaft member. The piston of the pushing member can be introduced into the longitudinal bore from the second end of the shaft member in order to push to implant out of the longitudinal bore. During implantation, the first end of the shaft member is brought into contact with the bone surface over the bore. The shaft member can not be inserted into the bore, because its diameter is slightly greater. Therefore, the shaft member serves to support the implant at its side walls during implantation whereas the pushing member presses the implant into the bore within the bone. As a result, the surgical instrument enables a proper and well aligned insertion of the implant, because the practitioner can easily control the insertion direction of the implant by means of the shaft member.

In order to further improve the support of the implant and its alignment during implantation, it is also possible to use a guide wire which extends through an internal bore of the implant and through an internal bore of the pushing member. With that, the implant is even supported when it is pushed out of the shaft member, because the guide wire may extend into the bore in the bone.

Alternatively, the guide wire can be fixed within the shaft member which extends at least partially at its center axis, and which extends through the first end of the shaft member so as to project by a length corresponding to the length of the implant. In this case, the pushing member has an internal slit so that it can be slided over the guide wire. The implant is sufficiently supported by the guide wire in order to avoid a misalignment of the implant within the bore of the bone during implantation.

With the surgical instrument according to the present invention, high forces can be applied to the implant during implantation, however, without damaging the implant due to a guided insertion into the bore of the bone. It is advantageous to provide the second end of the implant and the first end of the pushing member with flat surfaces so that the pressure is evenly distributed.

As a result, a ligament fixation near joint surface is achieved with a high mechanical strength of the ligament bone connection and with a good in vivo behavior. Further, since the implant is biodegradable, a removal is not necessary in case of revision surgery.

It is another primary object of the present invention to provide a system and an implant for bone reconstruction which enables a simplified procedure, and which can also be used for applications with medium and high loadings. Further, an early rehabilitation should be achieved.

The inventive implant and the inventive surgical instrument may also be used for bone reconstruction. In case of a collapsed bone structure, a bore is drilled from a side of the bone which is opposite to the collapsed surface. The collapsed surface is then pushed outwardly by directly introducing the implant into the bore. Therefore, the collapsed surface is reshaped by the pressure of the implant itself. As a result, the step of filling a void within the bone which was necessary for inserting a pestle, has been reduced to the insertion of the implant only. According to the invention, it is not necessary to fill a void after reshaping of the collapsed surface, because the implant remains in the bore.

DETAILED DESCRIPTION OF THE INVENTION

Figure 1:
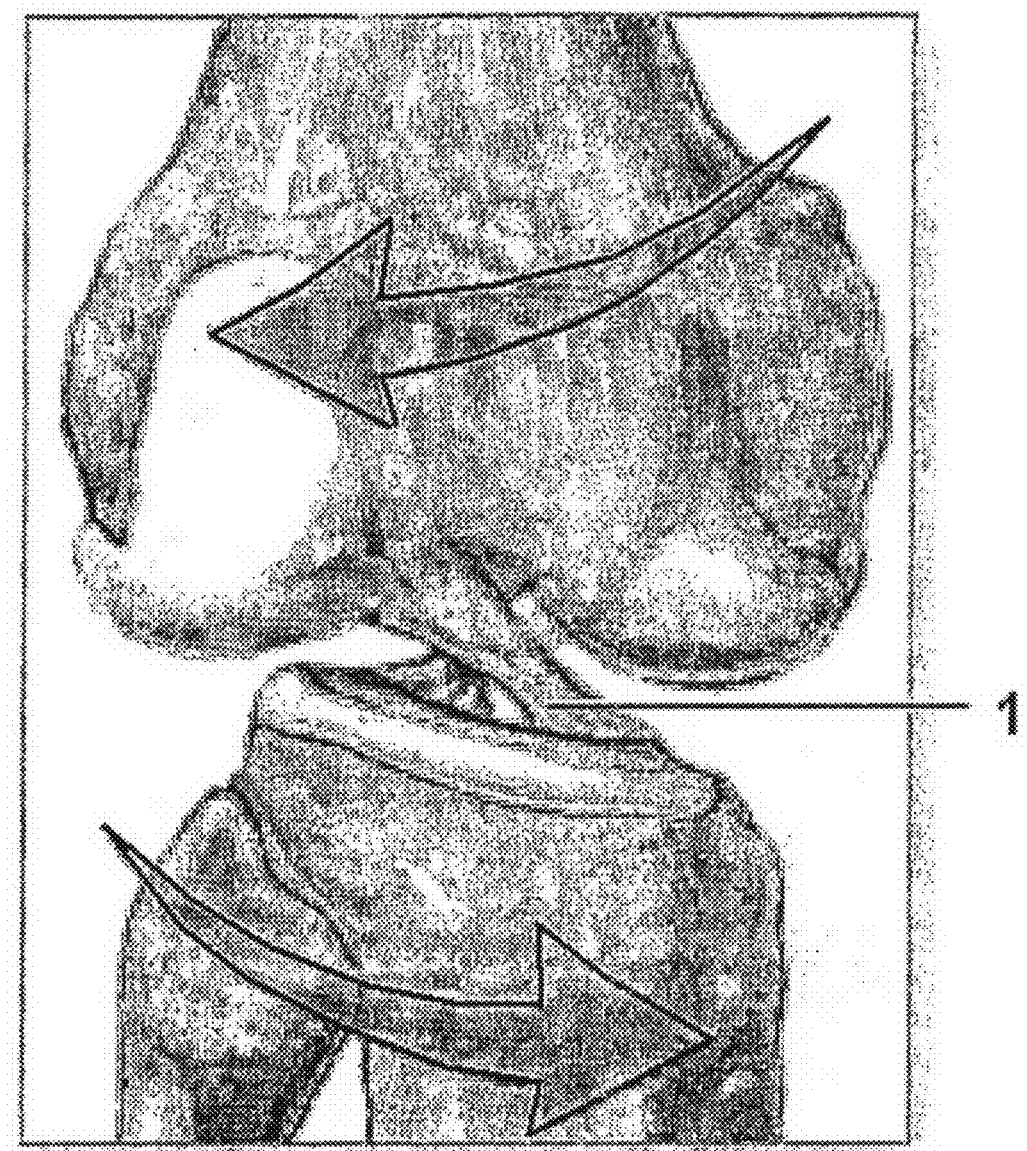
FIG. 1 shows the situation of a knee joint in which a rupture of an anterior cruciate ligament may occur.

FIG. 1 shows the situation of a knee joint in which a rupture of an anterior cruciate ligament 1 may occur e.g. in case of forcible external rotation and abduction of the knee or by increased contraction of the quadriceps muscle induced by forcible flection of the knee. For restoring the ruptured anterior cruciate ligament 1, a ligament plasty is necessary in which a ligament is connected to the bone structure. The present invention provides an implant, a surgical instrument and a system for reconstructing the anterior cruciate ligament. However, the present invention is not limited to this application; the present invention is also directed to the reconstruction of other ligament bone connections.

For reconstructing a ligament according to the present invention, the practitioner drills a bore into the bone. A natural ligament plasty (autograft, allograft or xenograft) with an optional small bone blocks at one or both ends or a synthetic ligament is then inserted into the bore. The ligament is pressed to the side walls of the bore by means of a pestle or trocar 2 so that the ligament which has viscoelastic properties, as well as the surrounding bone structure expand in radial direction. The inventive implant 4, 5, 6—as shown, for example, in FIGS. 5 to 7—is then pressed into the bore in order to securely fix the ligament to the bone by press fit or form fit. The other end of the ligament may finally be fixed to another bone by means of the inventive implant or by means of conventional methods.

Figure 2:
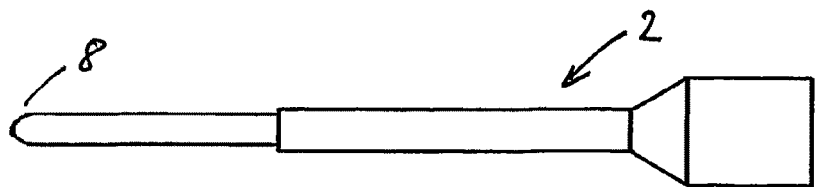
FIG. 2 shows a pestle of trocar of a system according to the present invention.

A pestle or trocar 2 according to a system of the present invention is shown in FIG. 2. The pestle 2 has a first end 8 with an outer diameter which is equal or slightly smaller than the outer diameter of the implant 4, 5, 6 so that the implant has to be inserted into the bore with a relatively high force in the order of for example greater than 500 N up to 3000 N.

For pressing the implant 4, 5, 6 into the bore for securely fixing the ligament, the inventive implant is designed to have a sufficient mechanical strength. The mechanical strength is sufficient to resist the pressure of a surgical instrument 9 for pressing the implant into the bore. Therefore, the implant preferably has a compression strength of at least 50 N/mm$^2$, in particular at least 80 N/mm$^2$. Therefore, in case of a diameter of the implant of 7 mm, a force of up to 1900 N or 3000 N, respectively, may be applied to the implant 4, 5, 6 for inserting the implant into the bore and for securely fixing the ligament by press fit or form fit. In view of theses forces, the inventive implant is also designed to resist shear stress of preferably at least 50 N/mm$^2$ so that the side walls of the implant are not sheared off during insertion into the bore.

Figure 11:
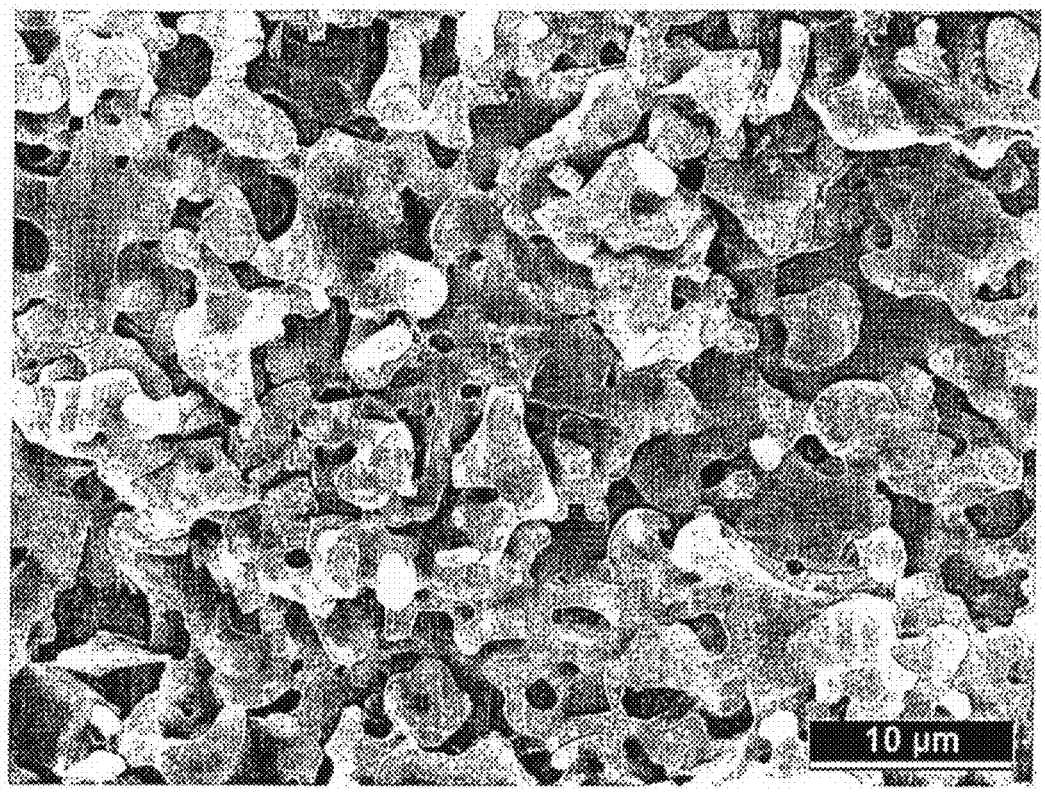
Figure 12:
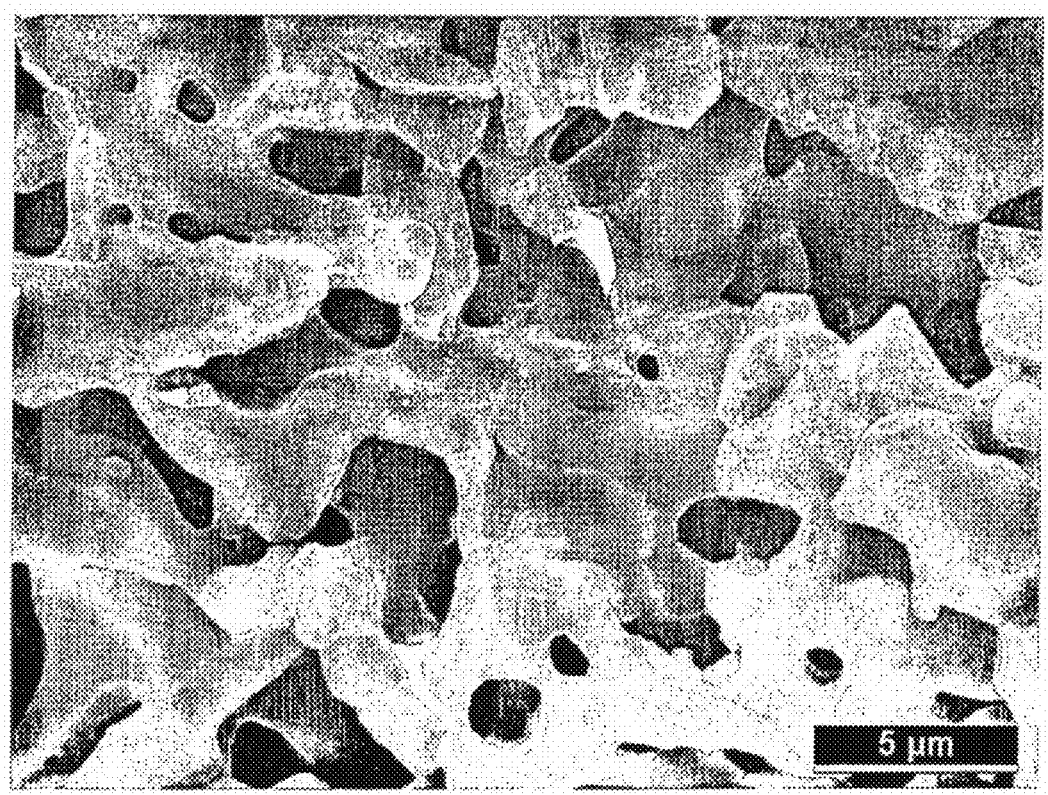

FIGS. 9 to 12 show the micro pore structure of a biodegradable material for an implant according to an embodiment of the present invention in various magnifications. The shown biodegradable material is β-tricalcium phosphate (β-Ca$_3$(PO$_4$)$_2$) having a micro pore structure with an average diameter ranging from 1 to 50 micrometers, in particular from 2 to 10 micrometers as shown in FIGS. 11 and 12. The microporosity accelerates the remodeling process by increasing the surface area an allowing for circulation of body fluids. Therefore, the porosity of the biodegradable material should be tailored to the desired period of biodegradation within a vital bone. On the other hand, the porosity of the biodegradable material is tailored to the mechanical strength required for securely fixing a ligament in a bore or hole by means of press fit or form fit. In order to achieve this mechanical strength, a porosity ranging from 25% to 50% by volume is preferred, in particular a porosity of about 40% by volume.

Figure 13:
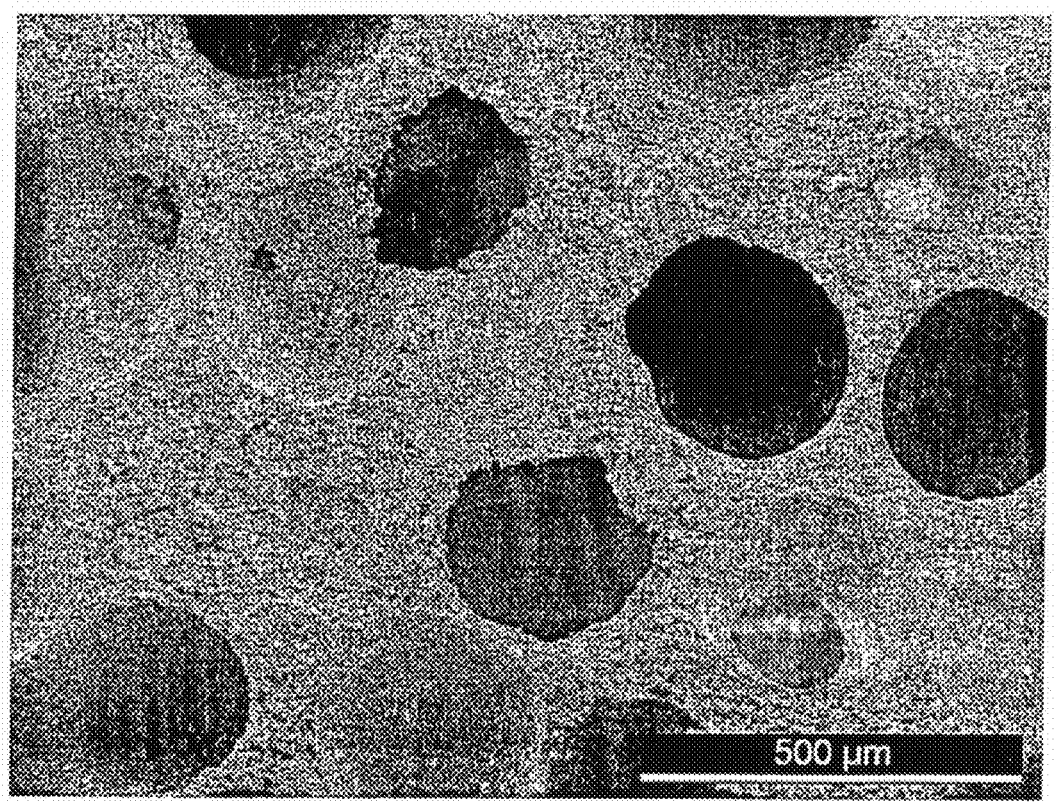
FIGS. 13 and 14 show a structure having macro pores and micro pores of a biodegradable material according to the prior art.
Figure 14:
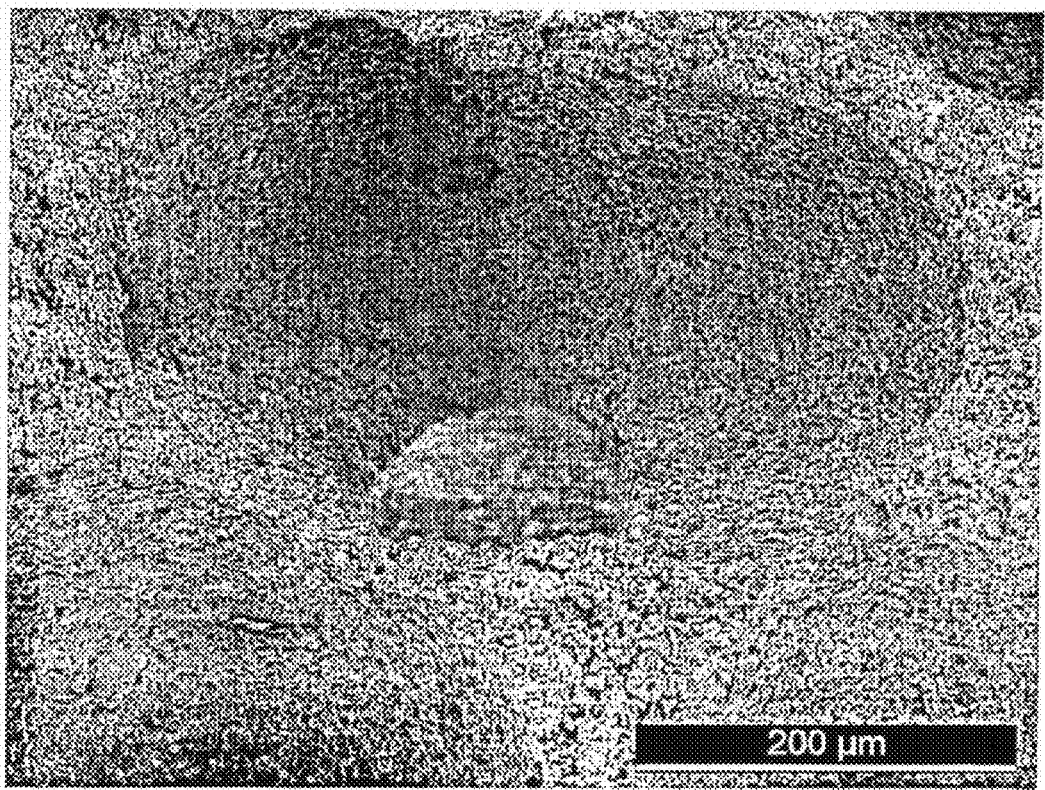

Preferably, at least part or all of the biodegradable material has no macro pores, which are defined in this patent application as having a diameter ranging from 100 to 500 micrometers. A biodegradable material such as β-tricalcium phosphate having macro pores and micro pores is shown in FIGS. 13 and 14. This ceramic material already has been suggested as material for filling voids in bones. However, since this material is highly fragile, and since the macro pores result in a porosity of the material of 60% to 70%, the use of β-tricalcium phosphate has been restricted according to the prior art to applications with minor loadings.

The micro pore structure is also advantageous in view of the mechanical properties of the inventive implant. The maximum tension stress at the end of a micro crack is reduced, because the radius of a micro pore is larger than the radius at the end of a crack in case of a material without micro pores. As a result, the tendency of a propagation of micro cracks is significantly reduced, in particular during the insertion of the implant.

In order to optimize the mechanical properties and the remodeling characteristics, the biodegradable material may have a gradient porosity, e.g. a lower porosity and a higher mechanical strength at the outer surface of the implant, and a higher porosity at the center of the implant. With that, a quicker remodeling of vital bone at the end of the healing process and a quicker rehabilitation is achieved.

The implant preferably consists only or at least 60% by weight, in particular at least 75% by weight of said biodegradable material which is suitable for remodeling into bone. The biodegradable material for remodeling into bone may be mixed with other biodegradable materials such as polysaccharides, dextran, starch, alginate, chitosan, proteins, albumin, collagen, gelatin, polyesters, different types of lactid acid, poly(glycolide) (PGA), poly(ϵ-caprolactone) (PCL), poly(β-hydroxyalkanoates) such as poly(β-hydroxybutyrate) (PB) and poly(β-hydroxyvalerate) (PHV), polyether-ester, poly(p-dioxanone) (PDO), polycarbonates, poly(trimethylene carbonate) (PTMC), poly(desaminotyrosyl tyrosine [ethyl ester]carbonate) PDTE), poly(amino acids), tyrosine-derived polycarbonates and polyarylates, poly(anhydrides), poly(SA-HAD anhydride), where SA is sebacic acid and HAD is hexadecandioic acid, poly(orthoesters), polyphosphoesters, polyphosphazenes, polyurethanes, polyesteramides, polyalkylenoxalates and polyalkylcyanoacrylates. Such a composition of materials can be designed to further improve the mechanical properties of the implant for specific applications. In particular, a composition with polymers reduces the fragility of the biodegradable material which is suitable for remodeling into bone.

The material of the implant may further contain one or more agents for facilitating osteogenesis. For this purpose, peptides, proteins, hormones, oligonucleotides, nucleic acids, steroids, antibiotics, antiseptics and vaccines are particularly suitable. The agent may be contained in the micro pore structure of the biodegradable material or in a polymer as a carrier for the agent in order to achieve a controlled release characteristic due to the degradation of the polymer.

Figure 5:
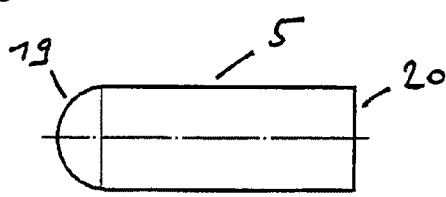
FIG. 5 shows an implant according to a first embodiment of the present invention.
Figure 6:
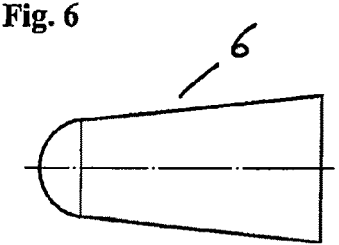
FIG. 6 shows an implant according to a second embodiment of the present invention.

FIG. 5 shows an implant 5 according to a preferred embodiment of the present invention which has a cylindrical shape. The outer diameter of the shown implant 5 is 7 mm and the length is 25 mm. A maximum friction is achieved with a cylindrical shape at the side walls of the implant so that pulling out of the ligament form the bore is avoided. However, also a conical shape of an inventive implant 6 is possible as shown in FIG. 6, in particular in case of a retrograde fixation of a ligament, i.e. at a side of the bone which is opposite to the joint. For that, an angle of the side walls with respect to the center axis of the implant of 2° to 15° is preferred, in particular about 7° to 8°.

Figure 7:
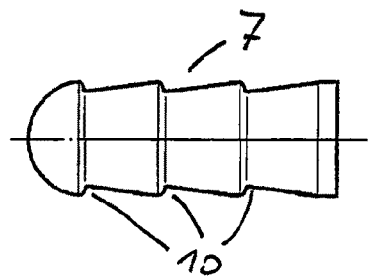
FIG. 7 shows an implant according to a third embodiment of the present invention.

The implant may further have circumferential or longitudinal grooves 10, as this is the case with the implant 7 having the fir tree structure shown in FIG. 7. The portions of the implant 7 having a larger diameter cause an increased pressure between the implant 7 and the surrounding vital bone structure. Such a locally increased pressure promotes the ingrowth of vital bone into the implant.

In view of the mechanical properties of the implant, it is preferred that the implant has no internal bores having a length exceeding 500 micrometers, and no bores as, for example, necessary with conventional implants in the shape of a dowel for fixing screws. On the other side, the implant of the present invention may be provided with an internal bore extending through the entire implant at its center axis in order to cooperate with a guide wire during implantation. This internal bore should have a small diameter in order not to reduce the mechanical properties of the implant, but to sufficiently support the implant over the guide wire in order to avoid a misalignment of the implant within the bore of the bone.

Figure 3:
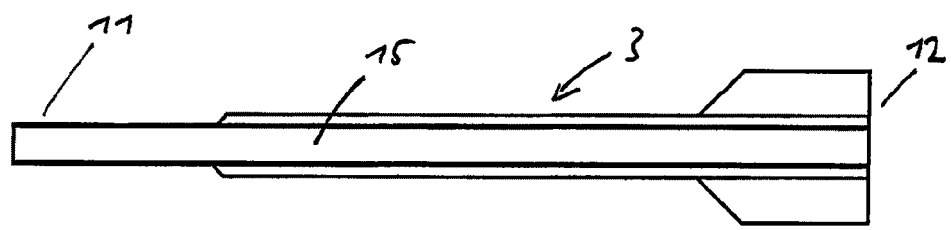
FIG. 3 shows a shaft member of a surgical instrument according to an embodiment of the present invention.
Figure 4:
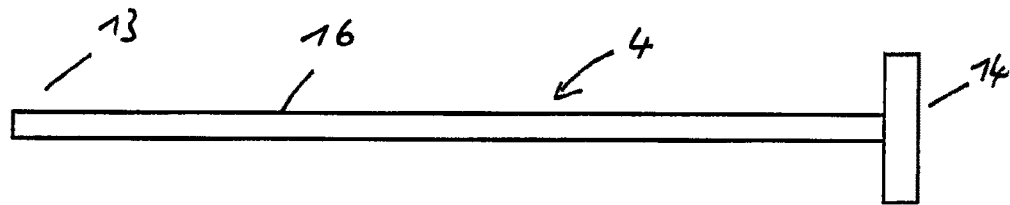
FIG. 4 shows a pushing member of a surgical instrument according to an embodiment of the present invention.

FIG. 3 shows a shaft member 3 of a surgical instrument according to a preferred embodiment of the present invention. The shaft member 3 has a first end 11, a second end 12 and a longitudinal bore 15, wherein the longitudinal bore 15 has an inner diameter. The surgical instrument of this embodiment further comprises a pushing member 4—shown in FIG. 4—having a first end 13, a second end 14 and a piston 16, wherein the piston 16 has an outer diameter which is smaller or equal than the inner diameter of the longitudinal bore 15 so that the piston 16 of the pushing member 4 can be slidably arranged within the longitudinal bore 15.

With the surgical instrument of this embodiment, an implant 5, 6, 7 can be inserted into the longitudinal bore 15 of the shaft member 3. The piston 16 of the pushing member 4 can be introduced into the longitudinal bore 15 from the second end 12 of the shaft member 3 in order to push to implant out of the longitudinal bore 15. During implantation, the first end 11 of the shaft member 3 is brought into contact with the bone surface over the bore. The shaft member can not be inserted into the bore, because its diameter is slightly greater. Therefore, the shaft member 3 serves to support the implant at its side walls during implantation whereas the pushing member 4 presses the implant into the bore within the bone. As a result, the surgical instrument enables a proper and well aligned insertion of the implant, because the practitioner can easily control the insertion direction of the implant 5, 6, 7 by means of the shaft member 3.

In order to further improve the support of the implant and its alignment during implantation, it is also possible to use a guide wire which extends through an internal bore of the implant and through an internal bore of the pushing member. With that, the implant is even supported when it is pushed out of the shaft member, because the guide wire may extend into the bore in the bone.

Figure 8:
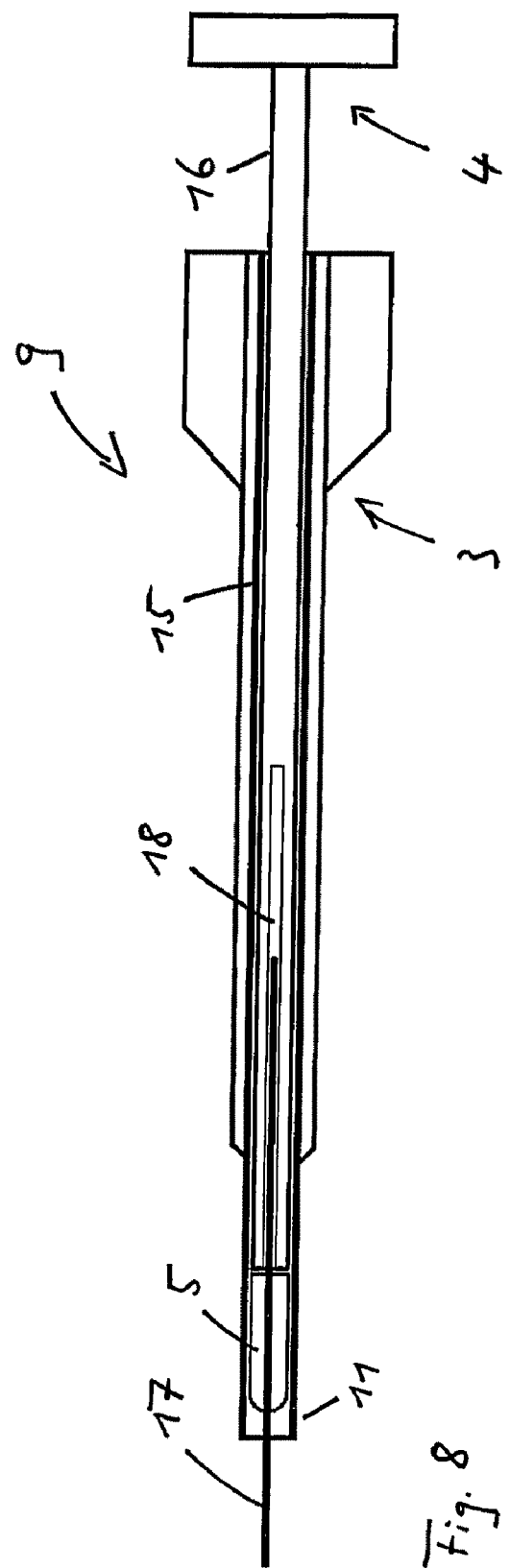
FIG. 8 shows a surgical instrument with an implant according to another embodiment of the present invention.
Figure 9:
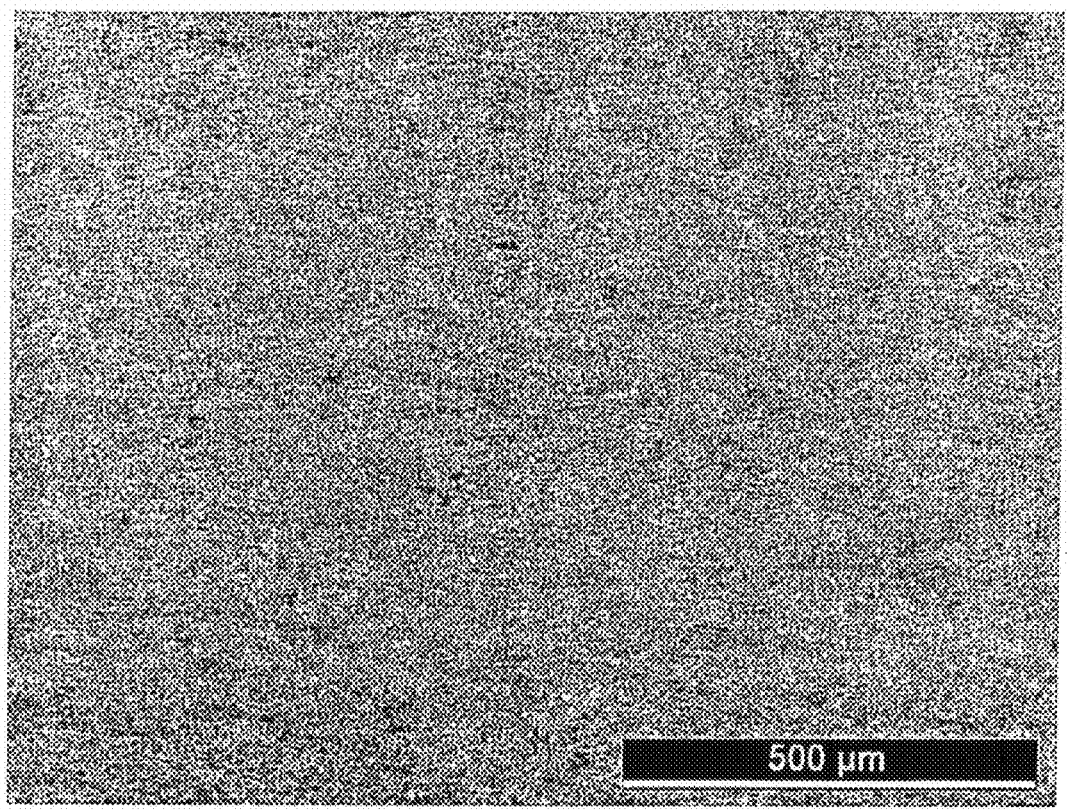
FIGS. 9 to 12 show the micro pore structure of a biodegradable material for an implant according to an embodiment of the present invention in various magnifications.
Figure 10:
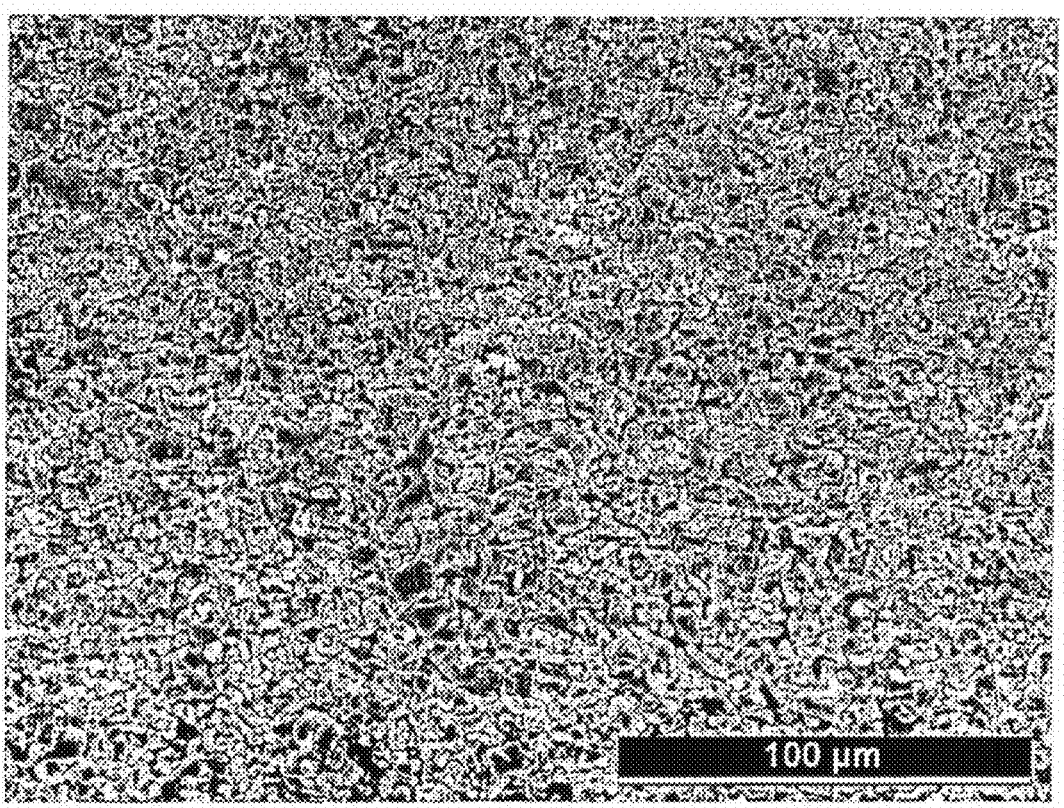

FIG. 8 shows a surgical instrument 9 with an implant according to another embodiment of the present invention. In this surgical instrument 9, a guide wire 17 is fixed within the shaft member 3 which extends at least partially at its center axis, and which extends through the first end 11 of the shaft member 3 so as to project by a length corresponding to the length of the implant 5. In this case, the pushing member 4 has an internal slit 18 so that it can be slided over the guide wire 17. The implant 5 having an internal bore is sufficiently supported by the guide wire in order to avoid a misalignment of the implant within the bore of the bone during implantation.

With the surgical instrument according to the present invention, high forces can be applied to the implant during implantation, however, without damaging the implant due to a guided insertion into the bore of the bone. It is advantageous to provide the second end 20 of the implant and the first end 13 of the pushing member with flat surfaces so that the pressure is evenly distributed. The first end 19 of the implant is preferably rounded in order to facilitate the insertion into the bore of the bone.

As a result, a ligament fixation near joint surface is achieved with the present invention with a high mechanical strength of the ligament bone connection and with a good in vivo behavior. Further, since the implant is biodegradable, a removal is not necessary in case of revision surgery.

The inventive implant and the inventive surgical instrument may also be used for bone reconstruction. In case of a collapsed bone structure, a bore is drilled from a side of the bone which is opposite to the collapsed surface. The collapsed surface is then pushed outwardly by directly introducing the implant into the bore. Therefore, the collapsed surface is reshaped by the pressure of the implant itself. As a result, the step of filling a void within the bone which was necessary for inserting a pestle, has been reduced to the insertion of the implant only. According to the invention, it is not necessary to fill a void after reshaping of the collapsed surface, because the implant remains in the bore.

The invention claimed is:

1. Implant for ligament and/or bone reconstruction wherein
the implant comprises a biodegradable material configured for remodeling into vital bone, and
the biodegradable material has a mechanical strength of at least 50 N/mm$^2$, a shear stress strength of at least 50 N/mm$^2$, comprises a micro pore structure with micro pores having an average diameter ranging from 1 to 50 micrometers and configured for securely fixing a ligament in a bore or hole of a bone by press or form fit and/or reshaping a collapsed surface of a bone into its original shape.

2. Implant according to claim 1, wherein said biodegradable material has a compression strength of at least 80 N/mm$^2$.

3. Implant according to claim 1, wherein the micro pores have an average diameter ranging from 2 to 10 micrometers.

4. Implant according to claim 1, wherein said biodegradable material has a porosity ranging from 25% to 50% by volume.

5. Implant according to claim 1, wherein said biodegradable material has a porosity of about 40% by volume.

6. Implant according to claim 1, wherein porosity of said biodegradable material is tailored to the mechanical strength required for securely fixing a ligament in a bore or hole by press or form fit.

7. Implant according to claim 1, wherein porosity of said biodegradable material is tailored to the desired period of biodegradation within the vital bone.

8. Implant according to claim 1, wherein said biodegradable material has a gradient porosity, in particular a lower porosity and a higher mechanical strength at the outer surface of the implant, and a higher porosity at the center of the implant.

9. Implant for ligament and/or bone reconstruction, wherein
the implant comprises a biodegradable material which is suitable to be remodeled into vital bone,
the biodegradable material has a mechanical strength for securely fixing a ligament in a bore or hole of a bone by press or form fit and/or reshaping a collapsed surface of a bone into its original shape, and
at least part of said biodegradeable material or all of said biodegradable material has no macro pores with a diameter ranging from 100 to 500 micrometers.

10. Implant according to claim 1, wherein said biodegradable material is selected from the group consisting of sintered or not sintered microporous ceramics such as hydroxyapatite, tricalcium phosphate, β-tricalcium phosphate (β-Ca$_3$(PO$_4$)$_2$), brushite, calcium sulfates, bioglass and combinations thereof.

11. Implant according to claim 1, wherein the implant comprises a composition of said degradable material and of a material selected from the group of: polysaccharides, dextran, starch, alginate, chitosan, proteins, albumin, collagen, gelatin, polyesters, different types of lactid acid, poly(glycolide) (PGA), poly(ε-caprolactone) (PCL), poly((β-hydroxyalkanoates) such as poly((β-hydroxybutyrate) (PHB) and poly ((β-hydroxyvalerate) (PHV), polyether-ester, poly (p-dioxanone) (PDO), poly carbonates, poly(trimethylene carbonate) (PTMC), poly (desaminotyrosyl tyrosine (ethyl ester) carbonate) (PDTE), poly(amino acids), tyrosine-derived polycarbonates and polyarylates, poly(anhydrides), poly(SA-HAD anhydride), where SA is sebacic acid and HAD is hexadecandioic acid, poly(orthoesters), polyphosphoesters, polyphosphazenes, polyurethanes, polyesteramides, polyalkylenoxalates and polyalkylcyanoacrylates.

12. Implant according to claim 1, wherein the implant is comprised of at least 60% by weight, in particular at least 75% by weight of said biodegradable material.

13. Implant according to claim 1, wherein the implant comprises one or more agents selected from the group of: osteogenesis facilitating agents, peptides, proteins, hormones, oligonucleotides, nucleic acids, steroids, antibiotics, antiseptics and vaccines.

14. Implant according to claim 1, wherein the implant is only composed of said biodegradable material.

15. Implant according to claim 1, wherein the implant has a cylindrical shape.

16. Implant according to claim 1, wherein the implant has a conical shape.

17. Implant according to claim 15, wherein the implant has circumferential or longitudinal grooves.

18. Implant according to claim 1, wherein implant has the shape of a screw or of a fir tree.

19. Implant according to claim 1, wherein the implant has an internal bore extending through the entire implant as its center axis for cooperating with a guide wire.

20. Implant according to claim 15, wherein the implant has no internal holes or bores.

21. Implant according to claim 15, wherein the implant has a rounded first end and a flat second end.

* * * * *